(12) United States Patent
Takahashi

(10) Patent No.: US 9,353,147 B2
(45) Date of Patent: *May 31, 2016

(54) METHOD FOR PRODUCING PEPTIDE

(71) Applicant: AJINOMOTO CO., INC., Chuo-ku (JP)

(72) Inventor: Daisuke Takahashi, Yokkaichi (JP)

(73) Assignee: AJINOMOTO CO., INC., Chuo-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/089,853

(22) Filed: Nov. 26, 2013

(65) Prior Publication Data

US 2014/0088291 A1 Mar. 27, 2014

Related U.S. Application Data

(63) Continuation of application No. PCT/JP2012/064074, filed on May 31, 2012.

(30) Foreign Application Priority Data

May 31, 2011 (JP) .................................. 2011-122798

(51) Int. Cl.
| | | |
|---|---|---|
| *C07K 5/04* | (2006.01) | |
| *C03B 19/12* | (2006.01) | |
| *C07K 1/06* | (2006.01) | |
| *C07K 1/02* | (2006.01) | |
| *C07K 5/083* | (2006.01) | |

(52) U.S. Cl.
CPC . *C07K 1/061* (2013.01); *C07K 1/02* (2013.01); *C07K 1/062* (2013.01); *C07K 5/0806* (2013.01)

(58) Field of Classification Search
None
See application file for complete search history.

(56) References Cited

U.S. PATENT DOCUMENTS

| 2004/0214989 A1 | 10/2004 | Chiba et al. | |
|---|---|---|---|
| 2009/0299103 A1 | 12/2009 | Chiba et al. | |
| 2010/0029904 A1* | 2/2010 | Chiba et al. | 530/331 |
| 2010/0240867 A1 | 9/2010 | Takahashi | |
| 2010/0249374 A1 | 9/2010 | Takahashi | |
| 2010/0261876 A1* | 10/2010 | Bray et al. | 530/324 |
| 2012/0108788 A1 | 5/2012 | Chiba et al. | |

FOREIGN PATENT DOCUMENTS

| JP | 2000-044493 | * | 2/2000 |
|---|---|---|---|
| JP | 2000-44493 A | | 2/2000 |
| WO | WO 03/018188 A1 | | 3/2003 |
| WO | WO 2006/104166 A1 | | 10/2006 |
| WO | WO 2007/034812 A1 | | 3/2007 |
| WO | WO 2007/122847 A1 | | 11/2007 |
| WO | WO 2010/104169 A1 | | 9/2010 |
| WO | WO 2010/113939 A1 | | 10/2010 |

OTHER PUBLICATIONS

Tamiaki et al., A Novel Protecting Group for Constructing Combinatorial Peptide Libraries, Bull. Chem. Soc. Jpn., 74, 733-738, 2001.*
Wade et al., DBU as an Na-Deprotecting Reagent for the Fluorenylmethoxycarbonyl Group in Continuous Flow Solid-Phase Peptide Synthesis, Pep. Res., vol. 4, No. 3, 1991, pp. 194-199.*
Watanabe et al., Cyclopentyl Methyl Ether as a New and Alternative Process Solvent, Org Proc. Res & Dev. 2007, 11, 251-258.*
"A new solvent for green chemistry," published online Jan. 12, 2011, http://manufacturingchemist.com.*
Tana et al., A practical solution-phase synthesis of an antagonistic peptide of TNF-a based on hydrophobic tag strategy, Chem. Commun., 2010, 46, 8219-8221.*
Eggen et al., A novel method for repetitive peptide synthesis in solution without isolation of intermediates, Jl. Peptide Sci, 11:633-641 (2005).*
Anna K. Tickler et al., "Improved Preparation of Amyloid-β Peptides Using DBU as N$^\alpha$-Fmoc Deprotection Reagent", Journal of Peptide Science, vol. 7, No. 9, Sep. 2001, pp. 488-494.
James E. Sheppeck et al., "A Convenient and Scaleable Procedure for Removing the Fmoc Group in Solution", Tetrahedron Letters, vol. 41, No. 28, Jul. 8, 2000, pp. 5329-5333.
Michael Beyermann et al., "Synthesis of Difficult Peptide Sequences: a Comparison of Fmoc-and BOC-technique", Tetrahedron Letters, vol. 33, No. 26, Jun. 23, 1992, pp. 3745-3748.
Hitoshi Tamiaki et al., "A Novel Protecting Group for Constructing Combinatorial Peptide Libraries", Bull. Chem. Soc. Jpn., 74, 2001, pp. 733-738.
U.S. Appl. No. 14/089,895, filed Nov. 26, 2013, Takahashi.
U.S. Appl. No. 14/244,433, filed Apr. 3, 2014, Takahashi.
D. Takahashi, et al., Tetrahedron Letters, vol. 53, pp. 1936-1939 (2012).

* cited by examiner

Primary Examiner — Satyanarayana R Gudibande
(74) Attorney, Agent, or Firm — Oblon, McClelland, Maier & Neustadt, L.L.P.

(57) ABSTRACT

The present invention provides a production method of peptide, which includes the following step (1).

(1) removing N-terminal Fmoc group of N-Fmoc C-protected amino acid or N-Fmoc C-protected peptide wherein a C-terminal carboxy group is protected by an anchor group derived from an anchor soluble in halogenated solvents or ether solvents, insoluble in polar solvents and having a molecular weight of not less than 300, with a non-nucleophilic organic base in a halogenated solvent or ether solvent to give a C-protected amino acid or C-protected peptide, neutralizing with an acid, adding N-Fmoc amino acid or N-Fmoc peptide, a condensing agent and a condensation accelerator to the reaction solution after neutralization, and condensing the N-terminal of the C-protected amino acid or C-protected peptide with N-Fmoc amino acid or N-Fmoc peptide to give an N-Fmoc C-protected peptide.

13 Claims, No Drawings

METHOD FOR PRODUCING PEPTIDE

TECHNICAL FIELD OF THE INVENTION

The present invention relates to a method capable of obtaining an object peptide with a high purity and a high yield by a convenient operation omitting an isolation and purification operation of an intermediate as much as possible, which is suitable for industrial production.

BACKGROUND OF THE INVENTION

As a production method of peptide besides a solid phase method and a liquid phase method, a production method using a protecting group (hereinafter to be also referred to as an anchor group) permitting a reaction in a homogeneous liquid phase, and, after changing the solvent composition after the reaction, performing isolation and purification merely by filtration and washing (hereinafter to be also referred to as an anchor method) has recently been proposed. The anchor method is a production method of peptide, wherein, in peptide synthesis and the like, a particular compound that shows reversible changes between a dissolved state and an undissolved (precipitated) state according to the changes of the solvent composition is used as a compound (anchor) that forms an anchor group for protecting the C-terminal and/or a side chain functional group of amino acid or peptide. Here, the anchor group means a protecting group that binds to a reactive substrate to make the substrate soluble in nonpolar solvents and capable of reaction in a liquid phase, and that precipitates on addition of a polar solvent to enable solid-liquid separation, thus showing both reactivity and convenience of working up. The anchor means a compound for forming an anchor group.

For example, patent document 1 and non-patent document 1 each disclose a method of using 3,4,5-tri(n-octadecyloxy) benzyl alcohol as a protective reagent for carboxy group and the like. In addition, patent documents 2-4 each disclose anchors such as 3,5-di(docosyloxy)benzyl alcohol, 2,4-di (docosyloxy)benzyl alcohol, trityl type compound and the like.

The present inventors have also developed a particular diphenylmethane compound (patent document 5) and a fluorene compound (patent document 6) as an anchor usable for the anchor method.

DOCUMENT LIST

Patent Documents patent document 1: JP-A-2000-44493
patent document 2: WO2006/104166
patent document 3: WO2007/034812
patent document 4: WO2007/122847
patent document 5: WO2010/113939
patent document 6: WO2010/104169

Non-Patent Document non-patent document 1: Bull. Chem. Soc. Jpn 74, 733-738 (2001)

SUMMARY OF THE INVENTION

Problems to be Solved by the Invention

The above-mentioned anchor method is a useful method in the organic synthetic methods such as peptide synthesis and the like, which shows advantages of both the solid phase reaction and the liquid phase reaction, such as convenient working up and possible scaling up, and draws attention from an industrial aspect. However, when sequential multistep synthetic reactions are needed such as in the peptide synthesis and the like, isolation and purification operations of concentration, precipitation by poor solvent, filtration, washing and drying need to be repeated in each step, so that undesirable side reactions will not occur in the next step. Since the high number of operation steps requires a large amount of time and cost, industrialization is prevented.

When an anchor other than the above-mentioned trityl type compound (patent document 4) and fluorene compound (patent document 6) is used, the same problem of by-production of diketopiperazine as in the liquid phase reaction occurs in the peptide synthesis when an isolation and purification operation including concentration, precipitation, filtration, washing and drying is performed after removal of the N-terminal temporary protecting group. Particularly, when a sequence having proline at the C-terminal or the second residue is contained or when two residues on the C-terminal are different optically active amino acids, for example, D-form and L-form amino acid and the like, by-production of diketopiperazine is remarkable. Furthermore, the present inventors have found that, in the anchor method, different from the liquid phase reaction, purification of peptide is difficult since the anchor itself, which was eliminated along with the by-production of diketopiperazine, also precipitates along with the object product in an isolation step of peptide protected by an anchor group, and the yield and purity of the object product decrease since an amino acid sequence derived from the eliminated anchor and a peptide having a different chain length are also by-produced.

The present invention has been made in view of the above-mentioned problems specific to the peptide synthesis by conventional anchor methods, and aims to provide an industrially useful production method of peptide, which suppresses conventionally problematic by-production of diketopiperazine, and incorporates a step that can be performed successively in one pot by omitting isolation and purification operations of an intermediate as much as possible.

Means of Solving the Problems

The present inventors have found that, in an elongation step of a peptide chain having a 9-fluorenylmethyloxycarbonyl group (hereinafter to be also referred to as Fmoc group) as a temporary protecting group of the N-terminal amino group of an amino acid or peptide, and an anchor group derived from an anchor as a protecting group of the C-terminal carboxy group, the steps up to the condensation reaction with N-Fmoc amino acid or N-Fmoc peptide can be performed successively in one pot by omitting a set of isolation and purification operations of concentration, precipitation, filtration, washing and drying from a temporary protecting group removal step by merely performing neutralization with an acid after removal of the Fmoc group with a non-nucleophilic organic base. In addition, they have found that said production method can suppress elimination of the anchor group by suppressing the by-production of diketopiperazine problematic in the peptide synthetic reaction by the conventional anchor method, which resulted in the completion of the present invention. The present invention is as follows.

[1] A method of producing a peptide, comprising:
(1) removing an N-terminal Fmoc group from (a) N-Fmoc C-protected amino acid or (b) an N-Fmoc C-protected peptide, with a non-nucleophilic organic base in a halogenated solvent or ether solvent to obtain a mixture comprising (a') a C-protected amino acid or (b') a C-protected peptide;

(2) neutralizing said mixture with an acid, to obtain a neutralized mixture;

(3) adding (c) an N-Fmoc amino acid or (d) an N-Fmoc peptide, a condensing agent and a condensation accelerator to said neutralized mixture; and (4) condensing the N-terminal of either of said (a') C-protected amino acid or said (b') C-protected peptide with either of said (c) N-Fmoc amino acid or said (d) N-Fmoc peptide to obtain (e) an N-Fmoc C-protected peptide, wherein, when said (1) removing an N-terminal Fmoc group comprises removing an N-terminal Fmoc group from (b) an N-Fmoc C-protected peptide, said (b) N-Fmoc C-protected peptide is different from said (e) N-Fmoc C-protected peptide, wherein a C-terminal carboxy group either of said (a) N-Fmoc C-protected amino acid or said (b) N-Fmoc C-protected peptide is protected by an anchor group derived from an anchor soluble in a halogenated solvent or ether solvent, insoluble in a polar solvent and having a molecular weight of not less than 300.

[2] The method according to [1], further comprising:

(5) precipitating said (e) N-Fmoc C-protected peptide with a polar solvent; and (6) obtaining said (e) N-Fmoc C-protected peptide by solid-liquid separation.

[3] The method according to [2], further comprising:

(7) removing N-terminal Fmoc group and/or C-terminal anchor group of said (e) N-Fmoc C-protected peptide.

[4] The method according to [1], wherein said anchor is a compound represented by formula (I):

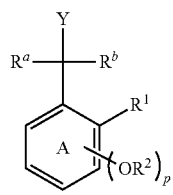

(I)

wherein:

$R^1$ is a hydrogen atom or, when $R^b$ is a group represented by the following formula (a), optionally forms a single bond together with $R^3$ to form a fluorene ring together with ring A and ring B;

each $R^2$ is independently an organic group having an aliphatic hydrocarbon group;

p is an integer of 1 to 4;

ring A optionally further has, in addition to $OR^2$, a substituent selected from the group consisting of a halogen atom, a $C_{1-6}$ alkyl group optionally substituted by a halogen atom, and a $C_{1-6}$ alkoxy group optionally substituted by a halogen atom;

$R^a$ is a hydrogen atom, or a phenyl group optionally substituted by a halogen atom; and $R^b$ is a hydrogen atom, or a group represented by formula (a):

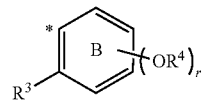

(a)

wherein:

* is the point of binding to the remainder of the molecule;

r is an integer of 0 to 4;

each $R^4$ is independently an organic group having an aliphatic hydrocarbon group;

$R^3$ is a hydrogen atom, or optionally forms a single bond together with $R^1$ to form a fluorene ring together with ring A and ring B; and ring B optionally further has, in addition to $OR^4$, a substituent selected from the group consisting of a halogen atom, a $C_{1-6}$ alkyl group optionally substituted by a halogen atom, and a $C_{1-6}$ alkoxy group optionally substituted by a halogen atom; and Y is a hydroxy group, a halogen atom, or NHR, wherein R is a hydrogen atom, an alkyl group or an aralkyl group.

[5] The method according to [4], wherein said compound represented by the formula (I) is a compound selected from the group consisting of:

3,4,5-tri(octadecyloxy)benzyl alcohol,
2,4-di(docosyloxy)benzyl alcohol,
4-methoxy-2-[3',4',5'-tri(octadecyloxy)benzyloxy]benzyl alcohol,
4-methoxy-2-[3',4',5'-tri(octadecyloxy)-cyclohexylmethyloxy]benzyl alcohol,
2-methoxy-4-[3',4',5'-tri(octadecyloxy)-cyclohexylmethyloxy]benzyl alcohol,
4-[3',4',5'-tri(octadecyloxy)cyclohexylmethyloxy]benzyl alcohol,
3,5-dimethoxy-4-[3',4',5'-tri(octadecyloxy)-cyclohexylmethyloxy]benzyl alcohol,
2,4-di(dodecyloxy)benzyl alcohol,
3,4,5-tri(octadecyloxy)benzylamine,
bis(4-docosyloxyphenyl)methanol,
bis(4-docosyloxyphenyl)methylamine, and
2-(12-docosyloxy-dodecyloxy)-9-(3-fluorophenyl)-9-bromofluorene.

[6] The method according to [1], wherein said non-nucleophilic organic base is selected from the group consisting of 1,8-diazabicyclo[5.4.0]-7-undecene, 1,4-diazabicyclo[2.2.2]octane, and 1,5-diazabicyclo[4.3.0]-5-nonene.

[7] The method according to [1], wherein said non-nucleophilic organic base is 1,8-diazabicyclo[5.4.0]-7-undecene.

[8] The method according to [1], wherein said acid is selected from the group consisting of methanesulfonic acid, trifluoromethanesulfonic acid, benzenesulfonic acid, p-toluenesulfonic acid anhydride, sulfuric acid, and a hydrogen chloride/ether solution.

[9] The method according to [1], wherein said acid is selected from the group consisting of methanesulfonic acid, trifluoromethanesulfonic acid, hydrogen chloride/diethyl ether, and hydrogen chloride/cyclopentyl methyl ether.

[10] The method according to [1], wherein said condensation accelerator is 1-hydroxybenzotriazole, ethyl 1-hydroxy-1H-1,2,3-triazole-5-carboxylate, 1-hydroxy-7-azabenzotriazole, O-(benzotriazol-1-yl)-N,N,N',N'-tetramethyluronium hexafluorophosphate, or O-(6-chlorobenzotriazol-1-yl)-N,N,N',N'-tetramethyluronium hexafluorophosphate.

[11] A method of producing a peptide, comprising:
(1) deprotecting an N-terminal of (a) an amino acid having protected N-terminal and protected C-terminal or (b) a peptide having protected N-terminal and protected C-terminal, with a heterocyclic compound having an amidine structure, to obtain a mixture comprising (a') a C-protected amino acid or (b') a C-protected peptide;
(2) neutralizing said mixture with an acid; and
(3) condensing either of said (a') a C-protected amino acid or said (b') C-protected peptide with (c) an N-protected amino acid or (d) an N-protected peptide.

[12] The method according to [11], wherein said protecting group removed in said (1) deprotecting is an Fmoc group.

Effect of the Invention

According to the production method of peptide of the present invention, a step of removing an Fmoc group which is a temporary protecting group of the N-terminal amino group of an amino acid or peptide, a neutralization step, and a subsequent condensation step with N-Fmoc amino acid or N-Fmoc peptide can be successively performed in one pot without isolation and purification operations of an intermediate. Therefore, a convenient and efficient production method of peptide, which is suitable for industrial production, can be provided. According to the present invention, moreover, in an elongation step of a peptide chain containing a particular sequence conventionally difficult to synthesize in a good yield due to the by-production of diketopiperazine, the by-production of an impurity peptide compound is suppressed and an object peptide compound can be produced with high purity and high yield.

DESCRIPTION OF EMBODIMENTS

Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferable methods and materials are described in the following. All publications and patents referred to in the present specification are hereby incorporated by reference so as to describe and disclose constructed products and methodology described in, for example, publications usable in relation to the described invention.

An amino acid which is a constitutional unit of a peptide produced by the method of the present invention is a compound having an amino group and a carboxy group in the same molecule, and may be a natural amino acid or non-natural amino acid, and an L form, a D form or a racemate. A peptide is synthesized by repeating a dehydration condensation step (condensation step) of an amino group of an amino acid component and a carboxy group of other amino acid component, according to the amino acid sequence of the peptide. Of the two amino acid components involved in the formation of the peptide bond, a component providing an amino group is hereinafter sometimes referred to as an amine component, and a component providing a carboxy group as an acid component.

The protecting group of the N-terminal amino group of an acid component to be used for the condensation step in the present invention is an Fmoc group.

In the present specification, the "N-Fmoc amino acid" or "N-Fmoc peptide" means an amino acid or peptide wherein an N-terminal amino group thereof is protected by an Fmoc group and a carboxy group is not protected.

In the present specification, the "C-protected amino acid" or "C-protected peptide" means an amino acid or peptide wherein the C-terminal carboxy group thereof is protected by forming an anchor group by condensing with an anchor soluble in halogenated solvents or ether solvents, insoluble in polar solvents and having a molecular weight of not less than 300 (e.g., benzyl compound, diphenylmethane compound or fluorene compound), and the N-terminal amino group is not protected.

In the present specification, the "N-Fmoc C-protected amino acid" or "N-Fmoc C-protected peptide" means the above-mentioned "C-protected amino acid" or "C-protected peptide" wherein the N-terminal amino acid is protected by an Fmoc group of a temporary protecting group.

Examples of the halogenated solvent in the present invention include halogenated hydrocarbons such as chloroform, dichloromethane, 1,2-dichloroethane, chlorobenzene and the like. The halogenated solvent may be a mixed solvent of two or more kinds. Among the halogenated solvents, chloroform and dichloromethane are particularly preferable.

Examples of the ether solvent in the present invention include 1,4-dioxane, cyclopentyl methyl ether (hereinafter sometimes to be referred to as CPME), tetrahydrofuran (hereinafter sometimes to be referred to as THF) and the like. The ether solvent may be a mixed solvent of two or more kinds. Among the ether solvents, CPME and THF are particularly preferable.

Examples of the polar solvent in the present invention include methanol, ethanol, isopropanol, acetonitrile, propionitrile, dimethylformamide, dimethylacetamide, dimethyl sulfoxide, water and the like, and a mixed solvent of two or more kinds of these. Of these, methanol or acetonitrile is preferably used. As the polar solvent in the present invention, methanol is preferable particularly from the aspect of practical utility.

One embodiment of the anchor soluble in halogenated solvents or ether solvents, insoluble in polar solvents and having a molecular weight of not less than 300 in the present invention is a compound represented by the following formula (I). Among such compounds, one having a molecular weight of not less than 400 is preferable.

The formula (I):

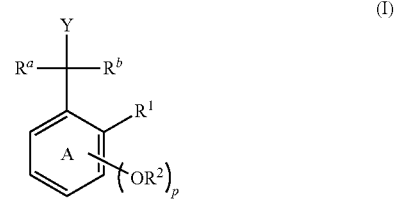

wherein
$R^1$ is a hydrogen atom or, when $R^b$ is a group represented by the following formula (a), optionally shows a single bond together with $R^3$ to form a fluorene ring together with ring A and ring B;
$R^2$ in the number of p is each independently an organic group having an aliphatic hydrocarbon group;
p is an integer of 1 to 4;
ring A optionally further has, in addition to $OR^2$ in the number of p, a substituent selected from the group consisting of a halogen atom, a $C_{1-6}$ alkyl group optionally substituted by a halogen atom, and a $C_{1-6}$ alkoxy group optionally substituted by a halogen atom;
$R^a$ is a hydrogen atom, or a phenyl group optionally substituted by a halogen atom; and
$R^b$ is a hydrogen atom, or a group represented by the formula (a):

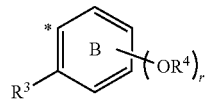

wherein * is a binding site;
r is an integer of 0 to 4;
$R^4$ in the number of r is each independently an organic group having an aliphatic hydrocarbon group;
$R^3$ is a hydrogen atom, or optionally shows a single bond together with $R^1$ to form a fluorene ring together with ring A and ring B; and
ring B optionally further has, in addition to $OR^4$ in the number of r, a substituent selected from the group consisting of a halogen atom, a $C_{1-6}$ alkyl group optionally substituted by a halogen atom, and a $C_{1-6}$ alkoxy group optionally substituted by a halogen atom; and
Y is a hydroxy group, NHR(R is a hydrogen atom, an alkyl group or an aralkyl group) or a halogen atom.

The anchor represented by the above-mentioned formula (I) is bound to a compound intended to be protected. That is, an anchor wherein Y is a hydroxy group, an —NHR group or a halogen atom protects a compound by condensing with a carboxy group on the C-terminal of amino acid or peptide and the like.

In the present specification, as the "alkyl group" for R, a straight or branched $C_{1-30}$ alkyl group can be mentioned. It is preferably a $C_{1-10}$ alkyl group, more preferably a $C_{1-6}$ alkyl group. Specific preferable examples include methyl, ethyl, propyl, isopropyl, butyl, isobutyl, sec-butyl, tert-butyl and the like, and methyl and ethyl are particularly preferable.

In the present specification, as the "aralkyl group" for R, a $C_{7-30}$ aralkyl group can be mentioned. It is preferably a $C_{7-20}$ aralkyl group, more preferably a $C_{7-16}$ aralkyl group ($C_{6-10}$ aryl-$C_{1-6}$ alkyl group). Specific preferable examples include benzyl, 1-phenylethyl, 2-phenylethyl, 1-phenylpropyl, naphthylmethyl, 1-naphthylethyl, 1-naphthylpropyl and the like, and benzyl is particularly preferable.

As R, a hydrogen atom, a $C_{1-6}$ alkyl group or a $C_{7-16}$ aralkyl group is preferable, a hydrogen atom, methyl, ethyl or benzyl is more preferable, and a hydrogen atom is particularly preferable.

In the present specification, the "halogen atom" is a fluorine atom, a chlorine atom, a bromine atom or an iodine atom. In the present specification, as the "halogen atom" for Y, a chlorine atom, a bromine atom or an iodine atom is preferable, and a bromine atom is more preferable.

In the present specification, the "organic group having an aliphatic hydrocarbon group" for $R^2$ or $R^4$ is a monovalent organic group having an aliphatic hydrocarbon group in a molecule structure thereof.

The "aliphatic hydrocarbon group" in the "organic group having an aliphatic hydrocarbon group" is a straight or branched saturated or unsaturated aliphatic hydrocarbon group, preferably an aliphatic hydrocarbon group having 5 or more carbon atoms, more preferably an aliphatic hydrocarbon group having 5 to 60 carbon atoms, further preferably an aliphatic hydrocarbon group having 5 to 30 carbon atoms, particularly preferably an aliphatic hydrocarbon group 10 to 30 carbon atoms.

The moiety of the "aliphatic hydrocarbon group" in the "organic group having an aliphatic hydrocarbon group" is not particularly limited, and may be present at the terminal (monovalent group), or other site (for example, divalent group).

Examples of the "aliphatic hydrocarbon group" include monovalent groups such as an alkyl group, a cycloalkyl group, an alkenyl group, a cycloalkenyl group, an alkynyl group and the like, and divalent groups derived therefrom, preferably monovalent groups such as a methyl group, an ethyl group, a propyl group, an isopropyl group, a butyl group, an isobutyl group, a sec-butyl group, a tert-butyl group, a pentyl group, a hexyl group, an octyl group, a decyl group, a dodecyl group, a lauryl group, a tridecyl group, a myristyl group, a cetyl group, a stearyl group, an arachyl group, a behenyl group, an oleyl group, an isostearyl group and the like, and divalent groups derived therefrom.

The moiety other than the "aliphatic hydrocarbon group" of the "organic group having an aliphatic hydrocarbon group" can be set freely. For example, it may have a moiety such as —O—, —S—, —COO—, —OCONH—, —CONH—, a hydrocarbon group (monovalent group or divalent group) and the like as a linker. Examples of the "hydrocarbon group" include an aliphatic hydrocarbon group, an aromatic-aliphatic hydrocarbon group, a monocyclic saturated hydrocarbon group, an aromatic hydrocarbon group and the like. Specifically, for example, monovalent groups such as an alkyl group, an alkenyl group, an alkynyl group, a cycloalkyl group, an aryl group, an aralkyl group and the like, and divalent groups derived therefrom are used. As the "alkyl group", a $C_{1-6}$ alkyl group and the like are preferable and, for example, methyl, ethyl, propyl, isopropyl, butyl, isobutyl, sec-butyl, tert-butyl, pentyl, hexyl and the like can be mentioned. As the "alkenyl group", a $C_{2-6}$ alkenyl group and the like are preferable and, for example, vinyl, 1-propenyl, allyl, isopropenyl, butenyl, isobutenyl and the like can be mentioned. As the "alkynyl group", a $C_{2-6}$ alkynyl group and the like are preferable and, for example, ethynyl, propargyl, 1-propynyl and the like can be mentioned. As the "cycloalkyl group", a $C_{3-6}$ cycloalkyl group and the like are preferable and, for example, cyclopropyl, cyclobutyl, cyclopentyl, cyclohexyl and the like can be mentioned. For example, the "aryl group" is preferably a $C_{6-14}$ aryl group and the like and, for example, phenyl, 1-naphthyl, 2-naphthyl, biphenylyl, 2-anthryl and the like can be mentioned. Of these, a $C_{6-10}$ aryl group is more preferable, and phenyl is particularly preferable. As the "aralkyl group", a $C_{7-20}$ aralkyl group is preferable and, for example, benzyl, 1-phenylethyl, 2-phenylethyl, 1-phenylpropyl, naphthylmethyl, 1-naphthylethyl, 1-naphthylpropyl and the like can be mentioned. Of these, a $C_{7-16}$ aralkyl group ($C_{6-10}$ aryl-$C_{1-6}$ alkyl group) is more preferable, and benzyl is particularly preferable. The "hydrocarbon group" may be substituted by a substituent selected from a halogen atom (a chlorine atom, a bromine atom, a fluorine atom, an iodine atom), an alkyl group having 1 to 6 carbon atoms and optionally substituted by one or more halogen atoms, an oxo group and the like.

In the "organic group having an aliphatic hydrocarbon group" constituting the $OR^2$ group or $OR^4$ group in the above-mentioned formula (I), plural "aliphatic hydrocarbon groups" may be present by branching and the like. When plural "aliphatic hydrocarbon groups" are present in the "organic group having an aliphatic hydrocarbon group", they may be the same or different.

In the "organic group having an aliphatic hydrocarbon group" for $R^2$ or $R^4$ in the above-mentioned formula (I), the lower limit of the total carbon number is preferably 5, more preferably 10, further preferably 12, still more preferably 14, especially preferably 16, and particularly preferably 20. On the other hand, in the "organic group having an aliphatic hydrocarbon group" for $R^2$ or $R^4$, the upper limit of the total carbon number is preferably 200, more preferably 150, further preferably 120, still more preferably 100, especially preferably 80, particularly preferably 60, particularly further preferably 40, and most preferably 30. The higher the carbon number, the better the crystallinity of the compound represented by the formula (I) in a polar solvent becomes, even when the peptide chain is a long chain.

Specific preferable examples of the "$OR^2$" group or "$OR^4$" group include dodecyloxy, cetyl oxy, octadecyloxy, docosyloxy, docosyloxy-dodecyloxy, triacontyloxy and the like. The "$OR^2$" group or "$OR^4$" group is present in a total number of p or r (p is an integer of 1 to 4 and r is an integer of 0 to 4), p is preferably 2 or 3, and r is preferably an integer of 0 to 2.

Specific preferable examples of the substituent optionally present in ring A or ring B in the above-mentioned formula (I) include a $C_{1-6}$ alkoxy group (e.g., a $C_{1-4}$ alkoxy group such as methoxy, ethoxy, propoxy, isopropoxy, butoxy, isobutoxy, sec-butoxy, tert-butoxy and the like), a $C_{1-6}$ alkyl group optionally substituted by one or more halogens (e.g., a $C_{1-6}$ alkyl group such as methyl, ethyl, propyl, isopropyl, butyl, isobutyl, sec-butyl, tert-butyl, pentyl, hexyl and the like, a halogen-substituted $C_{1-6}$ alkyl group such as trifluoromethyl, trichloromethyl and the like), and a halogen atom. Of these, a $C_{1-6}$ alkoxy group is preferable.

A preferable embodiment of the anchor represented by the above-mentioned formula (I) is a compound of the formula (I), wherein
Y is a hydroxy group;
$R^1$ is a hydrogen atom;
$R^2$ and/or $R^4$ are/is an aliphatic hydrocarbon group having 5 to 60 carbon atoms;
p is an integer of 1 to 3; and
r is an integer of 0 to 2.

Another preferable embodiment of the anchor represented by the above-mentioned formula (I) is a compound of the formula (I), wherein
Y is a hydroxy group;
$R^a$, $R^b$, and $R^1$ are each a hydrogen atom;
$R^2$ is an aliphatic hydrocarbon group having 5 to 60 carbon atoms; and
p is an integer of 1 to 3.

Another preferable embodiment of the anchor represented by the above-mentioned formula (I) is a compound of the formula (I), wherein
Y is a hydroxy group;
$R^a$, $R^b$, and $R^1$ are each a hydrogen atom;
$R^2$ is an alkyl group having 10 to 40 carbon atoms; and
p is 2 or 3.

Another preferable embodiment of the anchor represented by the above-mentioned formula (I) is a compound of the formula (I), wherein
Y is a hydroxy group;
$R^a$, $R^b$, and $R^1$ are each a hydrogen atom;
$R^2$ is an alkyl group having 12 to 30 carbon atoms; and
p is 2 or 3.

Another preferable embodiment of the anchor represented by the above-mentioned formula (I) is a compound of the formula (I), wherein
Y is a hydroxy group;
$R^a$, $R^b$, and $R^1$ are each a hydrogen atom;
$R^2$ is a benzyl group having 1 to 3 alkoxy groups having 12 to 30 carbon atoms; and
p is an integer of 1 to 3.

Another preferable embodiment of the anchor represented by the above-mentioned formula (I) is a compound of the formula (I), wherein
Y is a hydroxy group;
$R^a$, $R^b$, and $R^1$ are each a hydrogen atom;
$R^2$ is a cyclohexylmethyl group having 1 to 3 alkoxy groups having 12 to 30 carbon atoms; and
p is an integer of 1 to 3.

Preferable examples of the anchor soluble in halogenated solvents or ether solvents, insoluble in polar solvents and having a molecular weight of not less than 300 in the present invention include the following anchors.
3,4,5-tri(octadecyloxy)benzyl alcohol,
2,4-di(docosyloxy)benzyl alcohol,
4-methoxy-2-[3',4',5'-tri(octadecyloxy)benzyloxy]benzyl alcohol,
4-methoxy-2-[3',4',5'-tri(octadecyloxy)cyclohexylmethyloxy]benzyl alcohol,
2-methoxy-4-[3',4',5'-tri(octadecyloxy)cyclohexylmethyloxy]benzyl alcohol,
4-[3',4',5'-tri(octadecyloxy)cyclohexylmethyloxy]benzyl alcohol,
3,5-dimethoxy-4-[3',4',5'-tri(octadecyloxy)cyclohexylmethyloxy]benzyl alcohol,
2,4-di(dodecyloxy)benzyl alcohol,
3,4,5-tri(octadecyloxy)benzylamine,
bis(4-docosyloxyphenyl)methanol,
bis(4-docosyloxyphenyl)methylamine, and
2-(12-docosyloxy-dodecyloxy)-9-(3-fluorophenyl)-9-bromofluorene.

While the production method of the aforementioned anchor is not particularly limited, it can be produced from a starting material compound according to a method known per se (patent documents 1-6, non-patent document 1) or a method analogous thereto. A compound used as a starting compound, for example, halide corresponding to the group $R^2$ or $R^4$ in the formula (I) and the like can be obtained as a commercially available product or can be produced by a method known per se or a method analogous thereto.

An amino acid or peptide which is an acid component or an amine component to be used in the present invention often has, in addition to an amino group or carboxy group involved in the formation of a peptide bond, a functional group subjected to a dehydration condensation reaction, such as an amino group, a carboxy group, a hydroxy group and the like. Such functional group is distinguished from an amino group and a carboxy group forming a peptide bond of the main chain, and referred to as a side chain functional group. While the side chain functional group does not need to be always protected as long as it does not impair the gist of the present invention, it is preferably protected by an appropriate protecting group to prevent an undesirable side reaction during peptide bond formation by a dehydration condensation reaction and deprotection of an N-terminal amino groups.

The protecting group of the side chain functional group m is subject to a certain limitation on the combination with the N-terminal amino-protecting group, like the C-terminal carboxy-protecting group of the aforementioned amine component. That is, the protecting group of the side chain functional group needs to be maintained until the completion of the desired amino acid sequence, without being removed even under the removing conditions of an Fmoc group which is the protecting group of the N-terminal amino group. The protecting group is not particularly limited as long as the side chain functional group does not cause an undesirable side reaction during formation of the peptide bond by a dehydration condensation reaction and deprotection of the N-terminal amino group.

The protecting group of the side chain functional group is not particularly limited as long as it is stable under the deprotection conditions of an Fmoc group which is the protecting group of the N-terminal amino group (temporary protecting group). For example, the protecting groups described in PEPTIDE GOUSEI NO KISO TO JIKKENN (basis and experiment of peptide synthesis), published by Maruzen Co., Ltd. (1985), PROTECTIVE GROUPS IN ORGANIC SYNTHESIS, the third edition, published by JOHN WILLY&SONS (1999) and the like can be mentioned.

When the side chain functional group is a carboxy group, an ester-type protecting group, an amide-type protecting group, a hydrazide-type protecting group and the like can be mentioned.

As the ester-type protecting group, substituted or unsubstituted alkyl ester, and substituted or unsubstituted aralkyl ester are preferably used. As the substituted or unsubstituted alkyl ester, methyl ester, ethyl ester, tert-butyl ester, cyclohexyl ester, trichloroethyl ester, phenacyl ester and the like are preferably used. As the substituted or unsubstituted aralkyl ester, benzyl ester, p-nitrobenzyl ester, p-methoxybenzyl ester, diphenylmethyl ester, 9-fluorenylmethyl (Fm) ester, 4-picolyl (Pic) ester and the like are preferably used.

As the amide-type protecting group, unsubstituted amide, primary amide such as N-methylamide, N-ethylamide, N-benzylamide and the like, secondary amide such as N,N-dimethylamide, pyrrolidinylamide, piperidinylamide and the like, and the like are preferably used.

As the hydrazide-type protecting group, unsubstituted hydrazide, N-phenylhydrazide, N,N'-diisopropylhydrazide and the like are preferably used.

Of these, ester-type protecting groups which are stable under the deprotection conditions of an Fmoc group, such as t-butyl ester, substituted or unsubstituted benzyl ester and the like are preferably used, and substituted or unsubstituted benzyl ester is particularly preferably used since synthesis thereof is comparatively easy.

When the side chain functional group is an amino group, a urethane-type protecting group, an acyl-type protecting group, a sulfonyl-type protecting group and the like can be mentioned.

As the urethane-type protecting group, for example, a methoxycarbonyl group, an ethoxycarbonyl group, a tert-butoxycarbonyl (Boc) group, a benzyloxycarbonyl (Z) group and the like are used, and a methoxycarbonyl group, an ethoxycarbonyl group, a Boc group and the like are preferable. Of these, a Boc group is particularly preferably used since selective deprotection thereof is possible under mild acidic conditions.

As the acyl-type protecting group, for example, a formyl group, an acetyl group, a trifluoroacetyl group and the like are preferably used.

As the sulfonyl-type protecting group, for example, a p-toluenesulfonyl (Ts) group, a p-tolylmethanesulfonyl group, a 4-methoxy-2,3,6-trimethylbenzenesulfonyl group and the like are preferably used.

As for side chain functional groups other than those mentioned above, a protecting group stable under the deprotection conditions of an Fmoc group which is the protecting group (temporary protecting group) of the N-terminal amino group can be selected and used.

The side chain functional group can be deprotected as necessary after forming the object peptide bond.

Next, the production method of the present invention is explained. The production method of the present invention is a production method of peptide, which characteristically includes the following step (1).

(1) removing N-terminal Fmoc group of N-Fmoc C-protected amino acid or N-Fmoc C-protected peptide wherein a C-terminal carboxy group is protected by an anchor group derived from an anchor soluble in halogenated solvents or ether solvents, insoluble in polar solvents and having a molecular weight of not less than 300, with a non-nucleophilic organic base in a halogenated solvent or ether solvent to give a C-protected amino acid or C-protected peptide, neutralizing with an acid, adding N-Fmoc amino acid or N-Fmoc peptide, a condensing agent and a condensation accelerator to the reaction solution after neutralization, and condensing the N-terminal of the C-protected amino acid or C-protected peptide with N-Fmoc amino acid or N-Fmoc peptide to give an N-Fmoc C-protected peptide (N-terminal deprotection step and subsequent condensation step).

The N-Fmoc C-protected amino acid or N-Fmoc C-protected peptide to be used in step (1) in the production method of the present invention can be produced by the following step (a). In the following, step (a) is first explained before explanation on step (1).

Step (a) (C-terminal protection step)

In this step, an anchor soluble in halogenated solvents or ether solvents, insoluble in polar solvents and having a molecular weight of not less than 300 is condensed with a C-terminal of N-Fmoc amino acid or N-Fmoc peptide to give N-Fmoc C-protected amino acid or N-Fmoc C-protected peptide.

While the upper limit of the number of amino acid residues of the N-Fmoc peptide is not particularly limited as long as the N-Fmoc peptide to be used in this step is soluble in a solvent to be used in this step, the number of amino acid residues of N—Fmoc peptide is preferably not more than 100, more preferably not more than 50, still more preferably not more than 30.

The condensation reaction is preferably performed by dissolving anchor, N-Fmoc amino acid or N-Fmoc peptide and a catalytic amount of dimethylaminopyridine in a solvent, adding a condensing agent (and a condensation accelerator where necessary) and stirring the mixture.

This step is performed in a solvent that does not influence the reaction. The higher the solubility in the solvent becomes, the more superior the reactivity is expected to be. Therefore, a solvent showing high solubility of the aforementioned N-Fmoc amino acid or N-Fmoc peptide is preferably selected. Specifically, halogenated solvents such as chloroform, dichloromethane, 1,2-dichloroethane and the m like; and ether solvents such as 1,4-dioxane, cyclopentyl methyl ether, tetrahydrofuran and the like can be mentioned. Two or more kinds of these solvents may be used in a mixture in an appropriate ratio. In addition, aromatic hydrocarbons such as benzene, toluene, xylene and the like; nitriles such as acetonitrile, propionitrile and the like; ketones such as acetone, 2-butanone and the like; amides such as N,N-dimethylformamide and the like; sulfoxides such as dimethyl sulfoxide and the like may be mixed at an appropriate proportion with the above-mentioned halogenated solvent and ether solvents as long as the compound to be used for the production method of the present invention can be dissolved. Of these, chloroform, dichloromethane, cyclopentyl methyl ether or tetrahydrofuran is preferable, and chloroform is particularly preferable.

While the concentration of the N-Fmoc amino acid or N-Fmoc peptide in a solution in this step is not particularly limited as long as it is dissolved, it is preferably 1-30 wt %.

The amount of the N-Fmoc amino acid or N-Fmoc peptide to be used in this step can be 1-10 mol, preferably 1-5 mol, per 1 mol of the aforementioned anchor.

When Y is a hydroxy group, an ester bond is formed by adding a condensing agent and, where necessary, a condensation accelerator in a solvent that does not influence the reaction in the presence of a dimethylaminopyridine catalyst.

When Y is an —NHR group, an amide bond is formed by adding a condensing agent in the presence of a condensation accelerator.

When Y is a halogen atom, an ester bond is formed by adding a base such as diisopropylethylamine and the like in a solvent that does not influence the reaction.

As a condensation accelerator, 1-hydroxybenzotriazole (HOBt), ethyl 1-hydroxy-1H-1,2,3-triazole-5-carboxylate (HOCt), 1-hydroxy-7-azabenzotriazole (HOAt), 0-(benzotriazol-1-yl)-N,N,N',N'-tetramethyluronium hexafluorophosphate (HBTU), 0-(6-chlorobenzotriazol-1-yl)-N,N,N',N'-tetramethyluronium hexafluorophosphate (HCTU) and the like can be mentioned, with preference given to HOBt.

The amount of the condensation accelerator to be used is preferably 0.05-1.5 mol per 1 mol of the aforementioned anchor.

As a condensing agent, dicyclohexylcarbodiimide (DCC), diisopropylcarbodiimide (DIC), N-ethyl-N'-3-dimethylaminopropylcarbodiimide and hydrochloride thereof (EDC HCl), (benzotriazol-1-yloxy)tripyrrolidinophosphonium hexafluorophosphate (PyBop), O-(benzotriazol-1-yl)-N,N,N',N'-tetramethyluronium tetrafluoroborate (TBTU), 1-[bis(dimethylamino)methylene]-5-chloro-1H-benzotriazolium 3-oxide hexafluorophosphate (HCTU), O-benzotriazole-N,N,N',N'-tetramethyluronium hexafluorophosphate (HBTU) and the like can be mentioned.

The amount of the condensing agent to be used is, for example, 1-10 mol, preferably 1-5 mol, per 1 mol of the aforementioned anchor.

While the reaction temperature is not particularly limited as long as the reaction proceeds, it is preferably not less than −10° C., more preferably not less than 0° C., preferably not more than 50° C., more preferably not more than 30° C. The reaction time is, for example, 1-70 hr.

The N-Fmoc C-protected amino acid or N-Fmoc C-protected peptide contained in the thus-obtained reaction solution can be isolated by concentrating the reaction solvent under reduced pressure, adding the aforementioned polar solvent to allow for precipitation, solid-liquid separation (filtration) of the precipitate, and washing same with acetonitrile. Examples of the polar solvent to be used in this step include methanol, acetonitrile and the like, preferably methanol.

Step (1) (N-Terminal Deprotection Step and Subsequent Condensation Step)

In this step, an N-terminal Fmoc group of N-Fmoc C-protected amino acid or N-Fmoc C-protected peptide is removed by a treatment with a non-nucleophilic organic base to give a C-protected amino acid or C-protected peptide, which is then neutralized and, without an isolation and purification operation, C-protected amino acid or C-protected peptide and N-Fmoc amino acid or N-Fmoc peptide are subjected to dehydrating condensation.

While the upper limit of the number of the amino acid residues of the N-Fmoc C-protected peptide is not particularly limited as long as the N-Fmoc C-protected peptide to be used in this step is soluble in a solvent to be used in this step, the number of the amino acid residues of the N-Fmoc C-protected peptide is preferably not more than 100, more preferably not more than 50, further preferably not more than 30. While the upper limit of the number of amino acid residues of the C-protected peptide is not particularly limited as long as the C-protected peptide to be used in this step is soluble in a solvent to be used in this step, the number of amino acid residues of C-protected peptide is preferably not more than 100, more preferably not more than 50, still more preferably not more than 30.

In the following, step (1) is explained by dividing into step (1-1) (N-terminal deprotection step) and step (1-2) (condensation step).

Step (1-1) (N-Terminal Deprotection Step)

The Fmoc group is removed (deprotected) by treating same with a non-nucleophilic organic base in a halogenated solvent or ether solvent. The deprotection is performed in a solvent that does not influence the reaction.

As the non-nucleophilic base, 1,8-diazabicyclo[5.4.0]-7-undecene (DBU), 1,4-diazabicyclo[2.2.2]octane (DABCO), and 1,5-diazabicyclo[4.3.0]-5-nonene (DBN) and the like can be mentioned, DBU and DBN are preferable, and DBU is more preferable.

The halogenated solvent or ether solvents may be a mixed solvent of two or more kinds thereof. The halogenated solvent or ether solvent is preferably chloroform, dichloromethane, THF or CPME.

In this deprotection step, when nucleophilic organic base (secondary amine) such as dimethylamine, diethylamine, piperidine, morpholine and the like, which are widely used for removal of Fmoc group, are used in a nonpolar organic solvent such as chloroform and the like, the organic base in large excess is necessary to complete the reaction. When a nucleophilic base is used, a side reaction wherein an acid component is amidated occurs in the next condensation step. When the aforementioned non-nucleophilic base is used in this step, deprotection reaction is completed both in a halogenated solvent and an ether solvent. The amount of the non-nucleophilic base to be used is preferably not less than 0.8 equivalent, more preferably not less than 1 equivalent, preferably not more than 5 equivalents, more preferably not more than 3 equivalents, relative to the reactive substrate (N-Fmoc C-protected amino acid or N-Fmoc C-protected peptide).

To achieve one pot in this step, an organic base that exerts an adverse influence (side reaction such as deprotection of N-terminal of N-Fmoc amino acid or N-Fmoc peptide itself, which is a newly added acid component, and the like) on the next condensation reaction of C-protected amino acid or C-protected peptide and N-Fmoc amino acid or N-Fmoc peptide needs to be removed. In this step, therefore, it is essential to incorporate a neutralization step for addition of an acid to the reaction solution after the deprotection step.

Examples of the acid to be used for the neutralization step include methanesulfonic acid, trifluoromethanesulfonic acid, benzenesulfonic acid, p-toluenesulfonic acid anhydride, sulfuric acid, hydrogen chloride/ether solution and the like. Of these, methanesulfonic acid, trifluoromethanesulfonic acid, hydrogen chloride/diethyl ether and hydrogen chloride/cyclopentyl methyl ether are preferable.

The amount of the acid to be used is preferably not less than 0.5 mol, more preferably not less than 0.9 mol, preferably not more than 1.1 mol, more preferably not more than 1.0 mol, per 1 mol of the non-nucleophilic organic base.

While the reaction temperature of step (1-1) is not particularly limited as long as the reaction proceeds, it is preferably not less than −10° C., more preferably not less than 0° C., preferably not more than 50° C., more preferably not more than 30° C. The reaction time of step (1-1) is, for example, 1-70 hr.

Step (1-2) (Condensation Step)

In this step, N-Fmoc amino acid or N-Fmoc peptide, a condensing agent and a condensation accelerator are directly added to the reaction solution after the neutralization step in step (1-1) to perform condensation of the N-terminal of the C-protected amino acid or C-protected peptide with N-Fmoc amino acid or N-Fmoc peptide to give N-Fmoc C-protected peptide.

This step is performed using the condensing agent, condensation accelerator and the like described in the aforementioned step (a) and under the peptide synthesis conditions generally used in the field of peptide chemistry. A particularly preferable combination of a condensing agent and a condensation accelerator in this step is that of N-ethyl-N'-3-dimethylaminopropylcarbodiimide hydrochloride (EDC HCl) and 1-hydroxybenzotriazole (HOBt).

The amount of the condensation accelerator to be used is preferably not less than 0.05 mol, more preferably not less than 0.9 mol, preferably not more than 1.5 mol, more preferably not more than 1.1 mol, per 1 mol of the aforementioned C-protected amino acid or C-protected peptide.

The production method of the present invention may further contain step (2) (precipitation step) wherein N-Fmoc C-protected peptide is precipitated in a polar solvent, and obtained by solid-liquid separation, after step (1). Step (2) is explained in the following.

Step (2) (Precipitation Step)

In this step, the condensate (N-Fmoc C-protected peptide) obtained in the above-mentioned step (1) is isolated by changing the solvent, in which the condensate is dissolved (e.g., change of solvent composition, change of solvent kind), to allow for precipitation. That is, the reaction is performed under the conditions allowing dissolution of the condensate, the solvent is exchanged to cause precipitation of the condensate, followed by solid-liquid separation, and slurry washing to remove impurity. Evaporation of the solvent and the like may be performed before solvent exchange. As the solvent for exchange, a polar solvent such as methanol, acetonitrile and the like is used. That is, the reaction is performed under the conditions allowing dissolution of the compound and, after the reaction, as the solvent for exchange, for example, a halogenated solvent and the like are used for dissolution and a polar solvent such as methanol, acetonitrile and the like are used for precipitation.

The above-mentioned steps (1) and (2) may be repeated two times or more to obtain an N-Fmoc C-protected peptide having an elongated peptide chain. While the upper limit of the number of amino acid residues of the N-Fmoc C-protected peptide having an elongated peptide chain is not particularly limited as long as the N-Fmoc C-protected peptide is soluble in the solvent to be used in step (1), the number of the amino acid residues is preferably not more than 200, more preferably not more than 100, more preferably not more than 50.

The production method of the peptide of the present invention can further contain step (3) for removing the N-terminal Fmoc group and/or the C-terminal anchor group of the N-Fmoc C-protected peptide after the precipitation step (2). The N-terminal Fmoc group is removed according to, for example, the above-mentioned step (1).

The C-terminal anchor group is removed after the above-mentioned precipitation step (2) and after removal of the N-terminal Fmoc group, or before removal of the Fmoc group. As a result, the final object product peptide wherein the C-terminal of the peptide is —COOH (e.g., the aforementioned formula (I) wherein Y is a hydroxy group or a halogen atom), or —CONHR (e.g., the aforementioned formula (I) wherein Y is an NHR group) can be obtained.

When an anchor group derived from an anchor of the aforementioned formula (I) wherein Y is a hydroxy group or a halogen atom is selectively removed, deprotection is preferably performed by an acid treatment. As an acid to be used for the deprotection, trifluoroacetic acid (hereinafter to be referred to as TFA), hydrochloric acid, sulfuric acid, methanesulfonic acid, p-toluenesulfonic acid and the like can be mentioned, with preference given to TFA. As a solvent to be used for the deprotection, for example, chloroform, dichloromethane, 1,2-dichloroethane or a mixed solvent thereof and the like can be mentioned. The concentration of an acid to be used for the deprotection is, for example, 0.1 w/v %-5 w/v %.

It is also possible to remove an anchor group derived from an aromatic compound (anchor) of the aforementioned formula (I) wherein Y is a hydroxy group, an —NHR group, or a halogen atom, simultaneously with the protecting group of other side chain in a peptide. In this case, a conventional method used in the field, particularly peptide synthesis, is used, and a method including adding an acid and the like is preferably used. As the acid, TFA, hydrochloric acid, sulfuric acid, mesylic acid, tosylic acid, trifluoroethanol, hexafluoroisopropanol and the like are used. Of these, TFA is particularly preferable. The amount of the acid to be used is appropriately set according to the kind of the acid to be used, and an amount suitable for removing the anchor group is used. The amount of the acid to be used is preferably not less than 3 mol, more preferably not less than 5 mol, preferably not more than 100 mol, more preferably not more than 50 mol, per 1 mol of the N-Fmoc C-protected peptide. Along with such use, trifluoromethanesulfonic acid, trimethylsilyl trifluoromethanesulfonate, $BF_3$.etherate and the like can also be added as a further source of strong acid.

While the reaction temperature is not particularly limited as long as the reaction proceeds, for example, it is preferably 0° C.-50° C., more preferably 0° C.-30° C. The reaction time is, for example, 0.5-24 hr.

For confirmation of the progress of the reaction in the above-mentioned step (a), step (1) and step (3), a method similar to general liquid phase organic synthetic reaction can be applied. That is, thin layer silica gel chromatography, high performance liquid chromatography and the like can be used to trace the reaction.

EXAMPLES

The present invention is explained in more detail in the following by referring to Examples, which are not to be construed as limiting the scope of the present invention in any way. The reagents, apparatuses and materials used in the present invention are commercially available unless otherwise specified. In the present specification, when amino acid and the like are indicated by abbreviations, each indication is based on the abbreviation of the IUPAC-IUB Commission on Biochemical Nomenclature or conventional abbreviations in the art.

The anchor used in the Example can be produced by a method known per se (see the aforementioned patent documents 1-6, non-patent document 1) or a method analogous thereto, or method according to the following Reference Example 1, from a known starting material compound (or commercially available product).

Reference Example 1

Synthesis of 4-methoxy-2-[3',4',5'-tri(octadecyloxy)benzyloxy]benzyl alcohol (i) 3,4,5-Tri(octadecyloxy)benzyl alcohol (83.0 g, 90.8 mmol) was dissolved in chloroform (830 ml), thionyl chloride (21.6 g, 0.182 mol) was added at 0° C. and the mixture was stirred for 1.5 hr at room temperature. The solvent was evaporated, and the residue was crystallized from acetonitrile (800 ml) to give 3,4,5-tri(octadecyloxy)benzyl chloride as wet crystals (93.6 g).

(ii) 3,4,5-Tri(octadecyloxy)benzyl chloride (93.6 g, wet, <90.8 mmol), 2-hydroxy-4-methoxybenzaldehyde (15.2 g, 0.10 mol), potassium carbonate (31.4 g, 0.23 mol) were suspended in DMF (830 ml), and the mixture was stirred at 80° C. overnight. The reaction solution was dissolved in chloroform (1600 ml), and washed three times with 1N hydrochloric acid (800 ml), once with 5 wt % aqueous sodium hydrogen carbonate solution (800 ml) and once with 20 wt % brine (800 ml). The solvent was evaporated, and the residue was crystallized from methanol (800 ml), and washed with acetonitrile (800 ml) to give 4-methoxy-2-[3',4',5'-tri(octadecyloxy)benzyloxy]benzaldehyde (93.5 g, 89.2 mmol, yield 98%).

(iii) 4-Methoxy-2-[3',4',5'-tri(octadecyloxy)benzyloxy]benzaldehyde (93.5 g, 89.2 mmol) was dissolved in THF-methanol (1870 ml+94 ml), and sodium borohydride (4.05 g, 107 mmol) was added at 0° C. After stirring at room temperature for 1.5 hr, 0.2N hydrochloric acid (100 ml) was added at 0° C. to quench the reaction. About half the solvent was evaporated, the residue was dissolved in chloroform (2400 ml) and washed two times with 0.1N hydrochloric acid (1200 ml), once with 5 wt % aqueous sodium hydrogen carbonate solution (1200 ml) and once with 20 wt % brine (1200 ml). The solvent was evaporated, and the residue was crystallized from methanol (900 ml), and washed with acetonitrile to give 4-methoxy-2-[3',4',5'-tri (octadecyloxy)benzyloxy]benzyl alcohol (92.4 g, 88.0 mmol, yield 97% (vs 3,4,5-tri(octadecyloxy)benzyl alcohol)).

$^1$H-NMR (300 MHz, CDCl$_3$): δ 0.88 (9H, t, J=6.3 Hz, C$_{17}$H$_{34}$-Me), 1.15-1.40 (84H, br, C3',4',5'-OC$_3$H$_6$—C$_{14}$H$_{28}$—CH$_3$), 1.40-1.55 (6H, br, C3',4',5'-OC$_2$H$_4$—CH$_2$—C$_{15}$H$_{31}$), 1.70-1.85 (6H, m, C3',4',5'-OCH$_2$—CH$_2$—C$_{16}$H$_{33}$), 2.18 (1H, t, J=6.3 Hz, OH), 3.79 (3H, s, C4-O-Me), 3.90-4.03 (6H, m, C3',4',5'-O—CH$_2$—C$_{17}$H$_{35}$) 4.65 (2H, d, J=6.6 Hz, Ar—CH$_2$—OH) 4.97 (2H, s, Ar—O—CH$_2$—Ar), 6.47 (1H, dd, J=2.1, 8.1 Hz, C5-H), 6.53 (1H, d, J=2.4 Hz, C3-H), 6.60 (2H, s, C2',6'-H), 7.19 (1H, d, J=8.1 Hz, C6-H).

Example 1

Synthesis of dipeptide (Fmoc-Tyr(t-Bu)-Leu-OBzl (3,4,5-OC$_{18}$H$_{37}$)) from Fmoc-Leu-OBzl (3,4,5-OC$_{18}$H$_{37}$) wherein Deprotection Step (Removal Step of Fmoc Group), Neutralization Step and Dehydrating Condensation Step with Fmoc-Tyr(t-Bu)-OH are Successively Performed in One-Pot 3,4,5-tri(Octadecyloxy)benzyl alcohol (hereinafter sometimes indicated as Bzl (3,4,5-OC$_{18}$H$_{37}$)—OH) (3.0 g, 3.28 mmol) and Fmoc-Leu-OH (1.3 equivalents) were dissolved in chloroform, EDC HCl (1.4 equivalents) and dimethylaminopyridine (0.1 equivalent) were added under ice-cooling and the mixture was stirred. After completion of the reaction, the solvent was evaporated, MeOH (45 ml) was added and the mixture was stirred. The precipitate was collected by filtration, washed with acetonitrile and dried.

The obtained Fmoc-Leu-OBzl (3,4,5-OC$_{18}$H$_{37}$) was dissolved in chloroform, DBU (1.0 equivalent) was added under ice-cooling and the mixture was stirred. After completion of the deprotection, HCl/CPME solution (0.95 equivalent relative to DBU) was added, HOBt (1.0 equivalent) and Fmoc-Tyr(tBu)—OH (1.1 equivalents) were added, EDC HCl (1.2 equivalents) was added and the mixture was stirred. After completion of the condensation reaction, the solvent was evaporated, MeOH (45 ml) was added and the mixture was stirred. The precipitate was collected by filtration, washed with acetonitrile, and dried under reduced pressure to give Fmoc-Tyr(tBu)-Leu-OBzl (3,4,5-OC$_{18}$H$_{37}$) (4.04 g, 3.19 mmol, yield 97%).

TOF-MS(+)=1468.1.

The measurement device and conditions thereof used in Example 1 are as described below.
Measurement device: LCT Premier XE manufactured by Waters
Capillary voltage: 3000V
Sample cone voltage: 86V
Dissolution temperature: 350° C.
Source part temperature: 120° C.
LC part
Solvent: aqueous trifluoroacetic acid solution (trifluoroacetic acid concentration: 0.05 v/v %)-mixed solvent of MeCN and THF (MeCN concentration: 0.05 v/v %)
Column: AQUITY BEH C18 1.7 μm 2.1×50 mm
Temperature: 40° C.
Flow rate: 0.7 ml/min
Wavelength: 220 nm
Injection volume: 2 μl

Example 2

Synthesis of tripeptide (Fmoc-Ala-Pro-Gly-OBzl (3,4,5-OC$_{18}$H$_{37}$)) from Fmoc-Pro-Gly-OBzl (3,4,5-OC$_{18}$H$_{37}$) wherein Deprotection Step (Removal Step of Fmoc Group), Neutralization Step and Dehydrating Condensation Step with Fmoc-Ala-OH are Successively Performed in One Pot Fmoc-Pro-Gly-OBzl (3,4,5-OC$_{18}$H$_{37}$) (400 mg) obtained in the same manner as in Example 1 was dissolved in chloroform (5 ml), DBU (1.0 equivalent) was added under ice-cooling and the mixture was stirred. After completion of the deprotection, HCl/CPME solution (0.97 equivalent relative to DBU) was added, HOBt (1.0 equivalent) and Fmoc-Ala-OH (1.1 equivalents) and EDC HCl (1.2 equivalents) were added and the mixture was stirred. After completion of the condensation reaction, the solvent was evaporated, MeOH (5 ml) was added and the mixture was stirred. The precipitate was collected by filtration, washed with acetonitrile, and dried under reduced pressure to give Fmoc-Ala-Pro-Gly-OBzl (3,4,5-OC$_{18}$H$_{37}$) (415 mg). The content of Bzl (3,4,5-OC$_{18}$H$_{37}$)—OH in the obtained solid was measured under the same conditions as in Example 1 to find 0.9 mol % of the object product.

TOF-MS(+)=1361.5.

Example 3

Synthesis of tripeptide (Fmoc-Gly-Cys(Trt)-Tyr(t-Bu)—O-anchor Group) from Fmoc-Cys(Trt)-Tyr(t-Bu)—O-anchor Group Wherein Deprotection Step (Removal Step of Fmoc Group), Neutralization Step and Dehydrating Condensation Step with Fmoc-Gly-OH are Successively Performed in One Pot Fmoc-Cys(Trt)-Tyr(tBu)—OBzl (2-TOB-4-OMe) (9.0 g (4.90 mmol)) obtained in the same manner as in Example 1 except that 4-methoxy-2-[3',4',5'-tri(octadecyloxy)benzyloxy]benzyl alcohol (hereinafter sometimes to be indicated as HO-Bzl (2-TOB-4-OMe)) was used as a starting material was dissolved in chloroform (90 ml), DBU (870 mg, 1.2 equivalents) was added under ice-cooling and the mixture was stirred. After completion of the deprotection, methanesulfonic acid (522 mg, 0.95 equivalent relative to DBU) was added, HOBt (640 mg, 1.0 equivalent), Fmoc-Gly-OH (1.56 g, 1.1 equivalents), and EDC HCl (1.11 g, 1.2 equivalents) were added and the mixture was stirred. After completion of the condensation reaction, the solvent was evaporated, MeOH (90 ml) was added and the mixture was stirred. The precipitate was collected by filtration, washed with acetonitrile, and dried under reduced pressure to give Fmoc-Gly-Cys (Trt)-Tyr(tBu)—OBzl (2-TOB-4-OMe) (9.04 g, 4.77 mmol, yield 99%). The content of the decomposed Bzl(2-TOB-4-OMe)—OH in the obtained solid was measured under the same conditions as in Example 1 to find 1 mol % of the object product.

TOF-MS(+)=1893.2.

Example 4

Synthesis of Tripeptide(Fmoc-Ala-Pro-Gly-O-anchor Group) from Fmoc-Gly-O-anchor Group Wherein Deprotection Step (Removal Step of Fmoc Group), Neutralization Step and Dehydrating Condensation Step with Fmoc-Pro-OH are Successively Performed in One Pot, and Further, Peptide Chain Elongation Step Using Fmoc-Ala-OH is Also Performed in One Pot 2-(12-Docosyloxy-dodecyloxy)-9-(3-fluorophenyl)-9-bromofluorene (1.0 g) and Fmoc-Gly-OH (2 equivalents) were dissolved in chloroform, diisopropylethylamine (2 equivalents) was added and the mixture was stirred at 60° C. After completion of the reaction, the solvent was evaporated, methanol (5 ml) was added and the mixture was stirred. The precipitate was collected by filtration, washed with acetonitrile, and dried under reduced pressure. The solid was dissolved in chloroform, and DBU (1.5 equivalents) was added under ice-cooling to remove Fmoc. After completion of the reaction, HCl/CPME solution (0.95 equivalent relative to DBU) was added, HOBt (1.0 equivalent) and Fmoc-Pro-OH (1.1 equivalents) were added, EDC HCl (1.2 equivalents) was added, and the mixture was stirred. After completion of the condensation reaction, the solvent was evaporated, methanol (5 ml) was added and the mixture was stirred. The precipitate was collected by filtration, washed with acetonitrile, and dried under reduced pressure to give Fmoc-Pro-Gly-O-anchor group (1.28 g). The solid (1 g) was further subjected to the removal of Fmoc and subsequent condensation reaction by operations similar to those in the above to give Fmoc-Ala-Pro-GlyO-anchor group (1.04 g). The content of the decomposed 2-(12-docosyloxy-dodecyloxy)-9-(3-fluorophenyl)-9-fluorenol in the obtained solid was measured under the same conditions as in Example 1 to find 0.2 area % of the object product.

TOF-MS(+)=1232.5.

Experimental Example 1

Influence of Various Organic Bases and Solvents on by-Production of Diketopiperazine in Deprotection Reaction of Fmoc-Tyr(tBu)-Leu-OBzl (3,4,5-$OC_{18}H_{37}$) (Removal of Fmoc Group)

Experimental Method

The dipeptide (Fmoc-Tyr(tBu)-Leu-OBzl (3,4,5-$OC_{18}H_{37}$)) obtained in Example 1 was dissolved in chloroform or CPME, subjected to deprotection reaction using various bases for 2.5 hr, and the content of 3,4,5-tri(octadecyloxy)benzyl alcohol formed as a result of decomposition in conjunction with the by-production of diketopiperazine was measured by HPLC as a ratio relative to the yield of the object product.

Experimental Results

When non-nucleophilic DBU was used as an organic base, elimination of the anchor group was scarcely found in both an ether solvent THF and a halogenated solvent chloroform, and by-production of diketopiperazine could be suppressed. On the other hand, when nucleophilic diethylamine or piperidine was used, the amount of the eliminated anchor group increased remarkably, which indicates by-production of a large amount of diketopiperazine.

TABLE 1

| Solvent | Organic base for deprotection | 2.5 hr later (mol %) |
|---|---|---|
| THF | diethylamine (15 equivalents)/DBU (1 equivalent) | 18 |
| THF | piperidine (15 equivalents) | 80 |
| THF | DBU (1 equivalent) | 0.5 |
| chloroform | DBU (1 equivalent) | 0.2 |

Experimental Example 2

Comparison of One Pot Synthetic Method of the Present Invention (Method A: Example 2) and Conventional Sequential Synthetic Method (Method B, Method C) for by-production of diketopiperazine in Fmoc-Ala-Pro-Gly-OBzl (3,4,5-$OC_{18}H_{37}$) Synthetic Reaction

Experimental Method

The by-production rate of diketopiperazine when tripeptide (Fmoc-Ala-Pro-Gly-OBzl (3,4,5-$OC_{18}H_{37}$)) was produced by the following methods B, C was calculated from the measurement of the amount of the eliminated anchor, and compared.

Method B: Under the same conditions as in method A, the N-terminal Fmoc group of Fmoc-Pro-Gly-O-anchor group was removed using DBU (1 equivalent)/diethylamine (15 equivalents). After completion of the reaction, the mixture was neutralized with 0.95 equivalent of hydrogen chloride/CPME relative to DBU, concentrated and precipitated. Thereafter, the precipitate was dissolved and subjected to a condensation step with Fmoc-Ala to isolate tripeptide.

Method C: Under the same conditions as in method A, the N-terminal Fmoc group of Fmoc-Pro-Gly-O-anchor group was removed using diethylamine (50 equivalents). After completion of the reaction, and the mixture was subjected to concentration and precipitation. Thereafter, the precipitate was dissolved and subjected to a condensation step with Fmoc-Ala to isolate tripeptide.

Experimental Results

As compared to method A using DBU for removal of Fmoc group, method C using diethylamine required an excess amount of a base to complete the reaction in a halogenated solvent. Not only in the above-mentioned method C but also in method B using diethylamine to trap dibenzofulvene, elimination of the anchor group caused by the by-production of diketopiperazine could not be suppressed as shown in Table 2, even though the concentration and precipitation step was performed after removal of the Fmoc group.

TABLE 2

| Production method of tripeptide | Content of eliminated anchor in tripeptide (mol %) |
|---|---|
| Method A | 0.9 |
| Method B | 19 |
| Method C | 38 |

As shown above, it was found that, when diethylamine or piperidine, which is a nucleophilic organic base widely used as a deprotecting agent for Fmoc group, is used, the deprotection speed is slow in halogenated solvents or ether solvents as compared to DBU, which is a non-nucleophilic organic base, even when an excess amount of the organic base is used, and a side reaction of a reaction with an acid component to form amide occurs in the subsequent condensation step, thus decreasing the yield of the object product. Furthermore, when diethylamine or piperidine is used, the by-production of diketopiperazine during the deprotection cannot be suppressed. These results have clarified that use of about 0.8-5 equivalents of a non-nucleophilic and highly basic organic base such as DBU and the like is suitable for removing the Fmoc group, and further incorporation of a neutralization step enables steps up to the subsequent condensation step to be performed successively in one pot and suppression of the by-production of diketopiperazine.

INDUSTRIAL APPLICABILITY

According to the production method of peptide of the present invention, a step of removing an Fmoc group which is a temporary protecting group of the N-terminal amino group of an amino acid or peptide, a neutralization step, and a subsequent condensation step with N-Fmoc amino acid or N-Fmoc peptide can be successively performed in one pot without isolation and purification operations during the process. Therefore, a convenient and efficient production method of peptide, which is suitable for industrial production, can be provided. According to the present invention, moreover, since by-production of diketopiperazine can be suppressed, an object peptide compound can be produced with good purity for any sequence.

A differently expression method showing the characteristics of the production method of peptide of the present invention is described below.

An "immobilizing-protecting group" is defined as a "protecting group uninfluenced in a (deprotection step) and a (condensation step), and deprotected in a (final deprotection step)", and a general "protecting group" is defined as a "protecting group uninfluenced in a (condensation step), and deprotected in a (deprotection step)".

When a "production method of peptide by a method of immobilizing-protecting C-terminal and elongating N-terminal" is defined as a "production method of peptide comprising elongating a peptide chain in the N-terminal direction by repeating a step of N-terminal deprotection step of "N-terminal protected amino acid or peptide having immobilized and protected C-terminal (deprotection step) and a step of condensing with a novel N-terminal protected amino acid or peptide (condensation step)", Fmoc method and Boc method are included therein, and the Fmoc method is preferable.

Here, when an "improved successive method of immobilizing-protecting C-terminal and elongating N-terminal" is defined as a "method of immobilizing-protecting C-terminal and elongating N-terminal characterized by successively performing a (deprotection step) and a (condensation step) in a solution without purification by extraction, precipitation and the like on the way between these steps and purifying by a (precipitation step) after the completion of the (condensation step)", the production method of peptide of the present invention can also be expressed as follows.

[1] A production method of peptide by improved successive immobilization-protection of C-terminal and elongation of N-terminal, comprising a deprotection step by a heterocyclic compound having an amidine structure.

[2] The production method of peptide of [1], wherein the heterocyclic compound having the amidine structure is at least one kind selected from the group consisting of 1,8-diazabicyclo[5.4.0]-7-undecene, 1,4-diazabicyclo[2.2.2]octane, 1,5-diazabicyclo[4.3.0]-5-nonene.

[3] The production method of peptide of [1] or [2], further comprising a neutralization step with an acid after the deprotection step.

[4] The production method of peptide of [3], comprising a precipitation step after the condensation step.

[5] The production method of peptide of any one of [1]-[4], wherein the protecting group is an Fmoc group.

[6] The production method of peptide of any one of [1]-[4], comprising a final deprotection step.

The production method of peptide of the present invention can be further expressed in detail as follows.

(The First Step: C-Terminal Immobilizing-Protecting Step)

A step of producing N-terminal protected amino acid or peptide with immobilized and protected C-terminal by reacting C-terminal of an N-terminal protected amino acid or peptide with an immobilizing-protecting group.

(The Second Step: Deprotection Step)

A step of producing amino acid or peptide with immobilized and protected C-terminal by removing the N-terminal protecting group of the N-terminal protected amino acid or peptide with immobilized and protected C-terminal.

(The Third Step: Condensation Step)

A step of producing elongated N-terminal protected peptide with immobilized and protected C-terminal by condensing amino acid or peptide with immobilized and protected C-terminal and a novel N-terminal protected amino acid or peptide.

(The Fourth Step: Precipitation Step)

A step of purifying the elongated N-terminal protected peptide with immobilized and protected C-terminal by precipitating the elongated N-terminal protected peptide with immobilized and protected C-terminal in a polar solvent.

(The Fifth Step: Final Deprotection Step)

A step of producing an elongated peptide by removing the immobilized-protected C-terminal from the elongated N-terminal protected peptide with immobilized and protected C-terminal or elongated peptide with immobilized and protected C-terminal.

Since the above-mentioned second step, third step and fourth step are repeated as one set, the production method of peptide of the present invention specifically includes two cases as follows. m is a natural number, and "( . . . )×m times" means that the step in the parenthesis is repeated m times.

(Case 1) the first step→(the second step→the third step→the fourth step)×m times→the fifth step (Case 2) the first step→(the second step→the third step→the fourth step)×m times→the second step→the fifth step This application is based on a patent application No. 2011-122798 filed in Japan, the contents of which are incorporated in full herein.

The invention claimed is:

1. A method of producing a peptide, comprising:
   (1) removing an N-terminal Fmoc group from (a) N-Fmoc C-protected amino acid or (b) an N-Fmoc C-protected peptide, with a non-nucleophilic organic base in a halogenated solvent or ether solvent to obtain a mixture comprising (a') a C-protected amino acid or (b') a C-protected peptide;
   (2) neutralizing said mixture with an acid, to obtain a neutralized mixture;
   (3) adding (c) an N-Fmoc amino acid or (d) an N-Fmoc peptide, a condensing agent and a condensation accelerator to said neutralized mixture; and
   (4) condensing the N-terminal of either of said (a') C-protected amino acid or said (b') C-protected peptide with either of said (c) N-Fmoc amino acid or said (d) N-Fmoc peptide to obtain (e) an N-Fmoc C-protected peptide,
   wherein, when said (1) removing an N-terminal Fmoc group comprises removing an N-terminal Fmoc group from (b) an N-Fmoc C-protected peptide, said (b) N-Fmoc C-protected peptide is different from said (e) N-Fmoc C-protected peptide,
   wherein a C-terminal carboxy group either of said (a) N-Fmoc C-protected amino acid or said (b) N-Fmoc C-protected peptide is protected by an anchor group, and
   wherein said (1) removing, said (2) neutralizing, said (3) adding, and said (4) condensing are performed without any intervening isolation of said (a') C-protected amino acid or said (b') C-protected peptide, and
   wherein said anchor group is a group represented by formula (II):

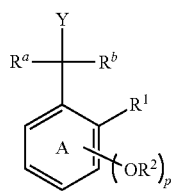

(I)

wherein:
   $R^1$ is a hydrogen atom or, when $R^b$ is a group represented by the following formula (a), optionally forms a single bond together with $R^3$ to form a fluorene ring together with ring A and ring B;
   each $R^2$ is independently an organic group having an aliphatic hydrocarbon group;
   p is an integer of 1 to 4;
   ring A optionally further has, in addition to $OR^2$, a substituent selected from the group consisting of a halogen atom, a $C_{1-6}$ alkyl group optionally substituted by a halogen atom, and a $C_{1-6}$ alkoxy group optionally substituted by a halogen atom;
   $R^a$ is a hydrogen atom, or a phenyl group optionally substituted by a halogen atom; and
   $R^b$ is a hydrogen atom, or a group represented by formula (a):

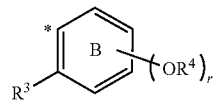

(a)

wherein:
   * is the point of binding to the remainder of the molecule;
   r is an integer of 0 to 4;
   each $R^4$ is independently an organic group having an aliphatic hydrocarbon group;
   $R^3$ is a hydrogen atom, or optionally forms a single bond together with $R^1$ to form a fluorene ring together with ring A and ring B; and
   ring B optionally further has, in addition to $OR^4$, a substituent selected from the group consisting of a halogen atom, a $C_{1-6}$ alkyl group optionally substituted by a halogen atom, and a $C_{1-6}$ alkoxy group optionally substituted by a halogen atom; and
   L represents a connection to the carbonyl group of said C terminus and is —O— or —N(R)—, wherein R is a hydrogen atom, an alkyl group, or an aralkyl group.

2. The method according to claim 1, further comprising:
   (5) precipitating said (e) N-Fmoc C-protected peptide with a polar solvent; and
   (6) obtaining said (e) N-Fmoc C-protected peptide by solid-liquid separation.

3. The method according to claim 2, further comprising:
   (7) removing N-terminal Fmoc group and/or C-terminal anchor group of said (e) N-Fmoc C-protected peptide.

4. The method according to claim 1, wherein said anchor group is derived from an anchor compound selected from the group consisting of:
   3,4,5-tri(octadecyloxy)benzyl alcohol,
   2,4-di(docosyloxy)benzyl alcohol,
   4-methoxy-2-[3',4',5'-tri(octadecyloxy)benzyloxy]benzyl alcohol,
   4-methoxy-2-[3',4',5'-tri(octadecyloxy)-cyclohexylmethyloxy]benzyl alcohol,
   2-methoxy-4-[3',4',5'-tri(octadecyloxy)-cyclohexylmethyloxy]benzyl alcohol,
   4-[3',4',5'-tri(octadecyloxy)cyclohexylmethyloxy]benzyl alcohol,
   3,5-dimethoxy-4-[3',4',5'-tri(octadecyloxy)-cyclohexylmethyloxy]benzyl alcohol,
   2,4-di(dodecyloxy)benzyl alcohol,
   3,4,5-tri(octadecyloxy)benzylamine,
   bis(4-docosyloxyphenyl)methanol,
   bis(4-docosyloxyphenyl)methylamine, and
   2-(12-docosyloxy-dodecyloxy)-9-(3-fluorophenyl)-9-bromofluorene.

5. The method according to claim 1, wherein said non-nucleophilic organic base is selected from the group consisting of 1,8-diazabicyclo[5.4.0]-7-undecene, 1,4-diazabicyclo[2.2.2]octane, and 1,5-diazabicyclo[4.3.0]-5-nonene.

6. The method according to claim 1, wherein said non-nucleophilic organic base is 1,8-diazabicyclo[5.4.0]-7-undecene.

7. The method according to claim 1, wherein said acid is selected from the group consisting of methanesulfonic acid, trifluoromethanesulfonic acid, benzenesulfonic acid, p-toluenesulfonic acid anhydride, sulfuric acid, and a hydrogen chloride/ether solution.

8. The method according to claim 1, wherein said acid is selected from the group consisting of methanesulfonic acid, trifluoromethanesulfonic acid, hydrogen chloride/diethyl ether, and hydrogen chloride/cyclopentyl methyl ether.

9. The method according to claim 1, wherein said condensation accelerator is 1-hydroxybenzotriazole, ethyl 1-hydroxy-1H-1,2,3-triazole-5-carboxylate, 1-hydroxy-7-azabenzotriazole, O-(benzotriazol-1-yl)-N,N,N',N'-tetramethyluronium hexafluorophosphate, or O-(6-chlorobenzotriazol-1-yl)-N,N,N',N'-tetramethyluronium hexafluorophosphate.

10. The method according to claim 1, wherein said N-Fmoc peptide has a length of not more than 100 amino acid residues.

11. The method according to claim 1, wherein said N-Fmoc peptide has a length of not more than 50 amino acid residues.

12. The method according to claim 1, wherein said N-Fmoc peptide has a length of not more than 30 amino acid residues.

13. The method according to claim 1, which comprises removing an N-terminal Fmoc group from (b) an N-Fmoc C-protected dipeptide, with a base which consists of a non-nucleophilic base.

* * * * *